US006274375B1

(12) United States Patent
McMinn, Jr.

(10) Patent No.: US 6,274,375 B1
(45) Date of Patent: Aug. 14, 2001

(54) SYSTEM AND METHOD FOR VENT HOOD CLEANING AND COMPREHENSIVE BIOREMEDIATION OF KITCHEN GREASE

(75) Inventor: Pearson Vernie McMinn, Jr., San Angelo, TX (US)

(73) Assignee: Allied Directives, LLC, Dallas, TX (US)

( * ) Notice: Subject to any disclaimer, the term of this patent is extended or adjusted under 35 U.S.C. 154(b) by 0 days.

(21) Appl. No.: 09/253,966

(22) Filed: Feb. 22, 1999

Related U.S. Application Data

(63) Continuation-in-part of application No. 08/678,104, filed on Jul. 11, 1996, now Pat. No. 5,874,292.

(51) Int. Cl.[7] .................................................. C12M 1/00

(52) U.S. Cl. .................................. 435/289.1; 435/289.1; 435/294.1; 210/167; 210/170; 210/191; 210/195.1; 210/201; 210/207; 210/513; 210/538

(58) Field of Search ............................ 435/286.5, 289.1, 435/294.1; 126/299 R, 299 F, 299 E; 210/167, 170, 191, 195.1, 201, 207, 512.1, 513, 538

(56) References Cited

U.S. PATENT DOCUMENTS 5,225,083 * 7/1993 Pappas et al. ....................... 210/606
5,360,555 * 11/1994 Batten ................................. 210/803
5,364,529 * 11/1994 Morin et al. ......................... 210/608
5,472,342 * 12/1995 Welsh, II et al. ................ 126/299 E
5,496,469 * 3/1996 Scraggs et al. ...................... 210/177

* cited by examiner

*Primary Examiner*—David A. Redding
(74) *Attorney, Agent, or Firm*—Mark A. Oathout

(57) ABSTRACT

A commercial and institutional kitchen retrofit system for 1. the automatic daily cleaning of commercial kitchen exhaust hoods and flues, 2. a low pressure, low volume, recirculating cleaning system designed for the removal of oily residue from hard surfaces and the accelerated bioremediation of the resulting collective hydrocarbon waste, 3. the collection and elimination of roof-top grease accumulations, 4. the systematic on site incubation and enhanced propagation of cultured, hydrocarbon specific, bacterial microorganisms in an automatically mixed aqueous solution containing PH neutral oxidizers and hydrocarbon base emulsifiers altogether, producing a regenerative, recyclable cleaning solution specifically developed for use in 5. and the automatic daily introduction of an oxygen enriched, microbe charged solution into kitchen drain lines, thereby reducing the stoppage of drains caused by the solidification of grease and ultimately promoting the biodigestation and reduction of accumulated grease in the main grease trap integral to the sewer system.

1 Claim, 12 Drawing Sheets

SYSTEM AND METHOD FOR VENT HOOD CLEANING AND COMPREHENSIVE BIOREMEDIATION OF KITCHEN GREASE

This application is a continuation-in-part of U.S. patent application Ser. No. 08/678,104 filed Jul. 11, 1996, now U.S. Pat. No. 5,874,292.

BACKGROUND OF THE INVENTION

1. Field of the Invention

This invention relates to a comprehensive, uniform, retrofit, commercial and institutional kitchen grease removal and bio-remediation system.

2. Description of Prior Art

In as much as grease residue is a by-product of certain forms of cooking, it is naturally understandable that numerous attempts have been made to address the myriad of problems associated with the accumulation of grease in higher volume commercial kitchens:

One area where grease buildup and its removal is most problematic is the exhaust hood, flue, roof surface adjacent to and surrounding the flue, and the kitchen drain lines and grease trap. Grease buildup in these areas is particularly critical in as much as it undermines the sanitary environment of the kitchen, increases the hazard of uncontrollable fires, generates foul odors, promotes insect and rodent infestation and is ultimately the primary cause of sewer stoppage. The generally accepted procedure for dealing with the exhaust hood grease problem is by manual periodic cleaning of the exhaust system when grease accumulations reach unacceptable levels. Grease is removed either manually with scrapers by the kitchen staff or by professional companies using steam and/or power spray washing equipment. In either case, the cleaning is usually done during off hours as it is an incredibly filthy and disruptive process. Handling the waste is a subsequent problem. Invariably, a good portion of the oily effluent ends up in the grease trap via the floor drains. This sudden surge in the volume of grease being discharged into the trap creates additional problems. These will be addressed later. However, the additional volume of greasy sludge shortens the intervals in the pumping (emptying) schedule for the grease trap and increases the frequency of clogged waste lines. The balance of the residue, if properly collected and contained must be disposed of, which, even in the best case scenario remains waste that is hazardous to the environment. An additional problem associated with manual or high pressure cleaning is the increased risk of possible inadvertent contamination of foodstuffs, utensils, and food prep surface areas resulting from failure to contain contaminates being carried in high volumes of water, airborne under pressure.

To avoid the many complications associated with this unpleasant manual procedure, various attempts have been made to devise automatic or self-cleaning hoods, which utilize permanent or removable tortuous air path baffle filters of various designs to catch the grease for removal by water spray. These vent hood systems are expensive and, regardless of their effectiveness, do nothing for the existing facility that cannot justify the complete replacement of a sound, fully functioning, conventional exhaust hood. Other pipe systems utilize fixed or rotating nozzle apparatuses extending along the axis of the exhaust duct (flue) and rely on the impingement of water spray under high pressure to remove grease buildup. Yet other systems are designed with elaborate pipe spray manifolds on wheels that are raised and lowered through the exhaust duct by pulleys and cables and provide coverage to the inside surface of the duct at terrific pressure. The intent is obviously to remove thick encrusted grease and sludge. That these systems utilize a relatively high volume of water in their operation is undeniable. One system in particular uses hot water in the cleaning process. Couple the cost of the water with the energy cost of heating it and it would only seem prudent to activate the system as infrequently as possible. A protracted cleaning schedule allows the daily accumulation of grease to build into the encrusted sludge these systems are obviously designed to address. Furthermore, the infrequent cleaning cycle and high volume of water produces the same waste disposal problems to contend with as the manual method previously discussed.

As with the self-cleaning hoods, it is apparent that these mechanical spray systems would most likely operate at optimum levels when installed in an exhaust duct tailored to be specifically compatible with the washing fixture. Otherwise, the washing fixture would have to be custom designed for each individual duct size and configuration. There seems to be a limitation in their utility in retrofit installations as universality is not apparent.

A search of prior art reveals several power spray washing systems for use inside confined areas such as tanks, pipes and exhaust systems. However, no system is found that provides thorough coverage of solution to adjacent surfaces at pressures less than 20 PSI and volumes as little as one-third gallon per minute. Additionally, no system was discovered that could be installed easily in retrofit and function universally well in a broad array of enclosure configurations having varying dimensions.

Regardless of the effectiveness of the various exhaust system washing devices, they commonly have no impact whatsoever on the grease that collects in and on the inside and outside surfaces of the exhaust fan unit typically mounted at the top of the flue. These grease accumulations generally drain downward from the exhaust fan and pool on the surface of the roof. This condition is undesirable in that, in addition to the obvious fire hazard, it sustains and promotes foul odors and ultimately undermines the integrity of most roofing systems. Hydrocarbons dissolve asphaltic roofing compounds and dramatically shorten roof life. The aspect of preparing or replacing a costly 10-year roofing system in 2 to 5 years is a sobering consideration indeed.

As with the exhaust washing systems, there are most certainly various prior art attempts at a solution to this problem. The exhaust fans have been fitted with collection buckets located below drainage holes drilled in the low point of the fan shroud. The grease that collects in the fan shroud drains through the hole and collects in the bucket below. These buckets require emptying on a regular basis or the grease overflows right back on the roof. Also, this approach does nothing to stop grease from flowing out between the base of the exhaust fan and the top of the flue to join the other grease accumulated on the outside of the fan itself on its downward flow to the roof.

Another prior art solution is to mount a gutter on the outside of the exhaust fan base skirt, which collects a portion of the grease in an integral box mounted on the gutter which is designed to separate grease and rainwater. Like the bucket solution, the collector box must be emptied manually or the grease overflows back onto the roof. Due to broad tolerances being acceptable in building practice, many exhaust flues are built to the exact size of the fan base, or out of square. Either situation leaves little or no free space between exhaust fan base skirts and flue housings for additional flashing components. For this reason, the gutter was designed to mount on the outside of the fan base skirt. Like other collectors, this design does not address the grease that flows outward between the top of the flue and the base of the exhaust fan.

Yet another attempt at addressing the problem has been to build a sand box on the roof surface surrounding the exhaust flue housing to collect the grease prior to its coming into contact with the roof. The ramifications of taking this approach are obvious in that oil and grease are lighter than water, therefore rain floats the grease out on the roof.

A more sophisticated prior art version of the sand box approach comprises an aluminum frame which lays on the roof surface and surrounds the flue housing containing a disposable fiber mesh trap type filter element which is intended to collect and retain the grease to the point of saturation and then be replaced. It would seem that a fiber filter saturated with flammable grease could be considered to have the properties of a wick waiting to be fired. This approach proves to be costly in as much as the filter elements and labor to replace them are not inexpensive.

The effectiveness of all prior art attempts reviewed that deal with the collection of grease is contingent on the timely emptying of the receptacle when full. Other than focusing primarily on keeping grease off the roof to some degree, these systems do little to address the other problems associated with rooftop grease including but not limited to fire hazards, rodent and insect infestation, foul odors associated with putrefying grease, and ultimately the final disposition of the grease itself.

Numerous prior art examples have been found that trap and treat grease with enzymes and/or bacterial spores. No doubt, various systems are effective to some extent in reducing the discharged volume of grease deposited in them.

Some prior art deals with the manual introduction of microbes into the sewer drain lines and grease traps of commercial kitchens. More specifically, floor drain covers are repaired to preclude foreign matter from entering the drain lines and microbes are introduced. However, this is a manual process which is obviously done on a periodic schedule. In as much as it is difficult to eliminate the use of cleaners and other chemicals including but not limited to chlorine, which is toxic to microbial life, in the day-to-day operation of a food service facility, the effectiveness of infrequent treatment is easily undermined. The only possible way of assuring enhanced bioremediation is through the daily metered injection of fresh, healthy hydrocarbon-specific microorganisms into the primary floor drain lines and grease trap. No known system exists specifically designed for this purpose.

SUMMARY OF THE INVENTION

None of the prior art grease trap devices, being primarily of singular purpose in their design, offer an intentional multiplicity of functions beginning with A. A controlled environment designed specifically for the enhanced and sustained on-site (point of use) propagation of cultured hydrocarbon specific microflora. B. Capable of cycling large volumes of rainwater through the system without purging or flushing the high or low gravity liquid out of the system. C. Support an integral systematic recirculating pressure cleaning apparatus. Nor has any device been discovered that in addition to collectively integrating and providing all the systematic functions listed in A, B and C, also D. Acts as a cleaning solution reclaimer, rejuvenator and recycler and E. Systematically inoculates the sewer drain lines and primary grease trap automatically on a timed daily basis from a never ending perpetual supply of on-site propagated hydrocarbon-specific microorganisms to ultimately reduce the total volume of grease waste accumulated from cooking operations that is discharged into the sewer system. In as much as microbiological treatment of hydrocarbon waste has proven to be advantageous it has also been established that micro-organic life itself is vulnerable to a broad spectrum of toxic chemicals and less than ideal environmental conditions. For this reason, the accepted practice for the food service industry is to manually charge grease traps and/or drain lines monthly to re-establish microbe colonies being killed daily by toxic chemicals being discharged into the grease traps via the sewer system usually stemming from mopping, dishwashing and other cleaning operations. The standard procedure involves culturing hydrocarbon specific microorganisms in a laboratory and then bringing the culture to the point of use for manual introduction into the target system, thereby replenishing the microflora periodically. However, microbes are quite prolific given an ideal environment conducive to enhanced propagation. Therefore, an on-site system that by design cannot be purged by large volumes of flowing water, is not subjected to contaminates by being located in line with sewer waste water and is climatically stable seems needed and at this point unavailable.

The object of this invention deals with a comprehensive process for the timed systematic collection and bioremediation of kitchen grease that begins with the retrofit installation in a commercial kitchen of an integrated system of technology that includes:

a. A bio-reactive fluid reclaim unit comprised of a series of tanks, pumps, filters, timer, solenoid valves, float valves, contactors, heat elements, T-stats and the necessary wiring harnesses and fluid connectors to facilitate its operation.

b. A universally adaptable low volume, low pressure spray boom assembly, comprising a piping system and rotary spray nozzles designed to operate at pressures of 20 PSI or less and volumes as low as one third gallon per minute.

c. A baffle system, for universal retrofit installation in commercial kitchen exhaust hoods that, in addition to allowing free air passage and collecting the fall back grease as traditional baffles do, also prohibits the passage of aqueous splatter as might result from the cleaning cycle.

d. A fluid return sump assembly, and optional universal hood gutter, to collect washing fluid and hydrolyzed grease residue resultant of a cleaning process.

e. An automatic fluid return sump assembly, and related piping system to return the washing fluid and hydrolyzed grease residue to the Bio-reactive fluid reclaim unit.

f. A makeup solution injector reservoir, containing a microbe reserve and supply of PH neutral surfactant/disbursant/oxidizing solution for timed and metered daily injection into the system via the fluid return sump assembly.

g. A fluid collector manifold/fan mount adaptor, that mounts on top of the flue above the roof line between the flue and the base of the exhaust fan.

h. A drain line, connecting the gutter/ manifold to the circulation/bioremediation unit.

i. A drain line, connecting the bio-reactive, fluid reclaim unit to the nearest plumbing waste vent or vents common to the kitchen floor drain system.

DETAILED DESCRIPTION

Figure 6:
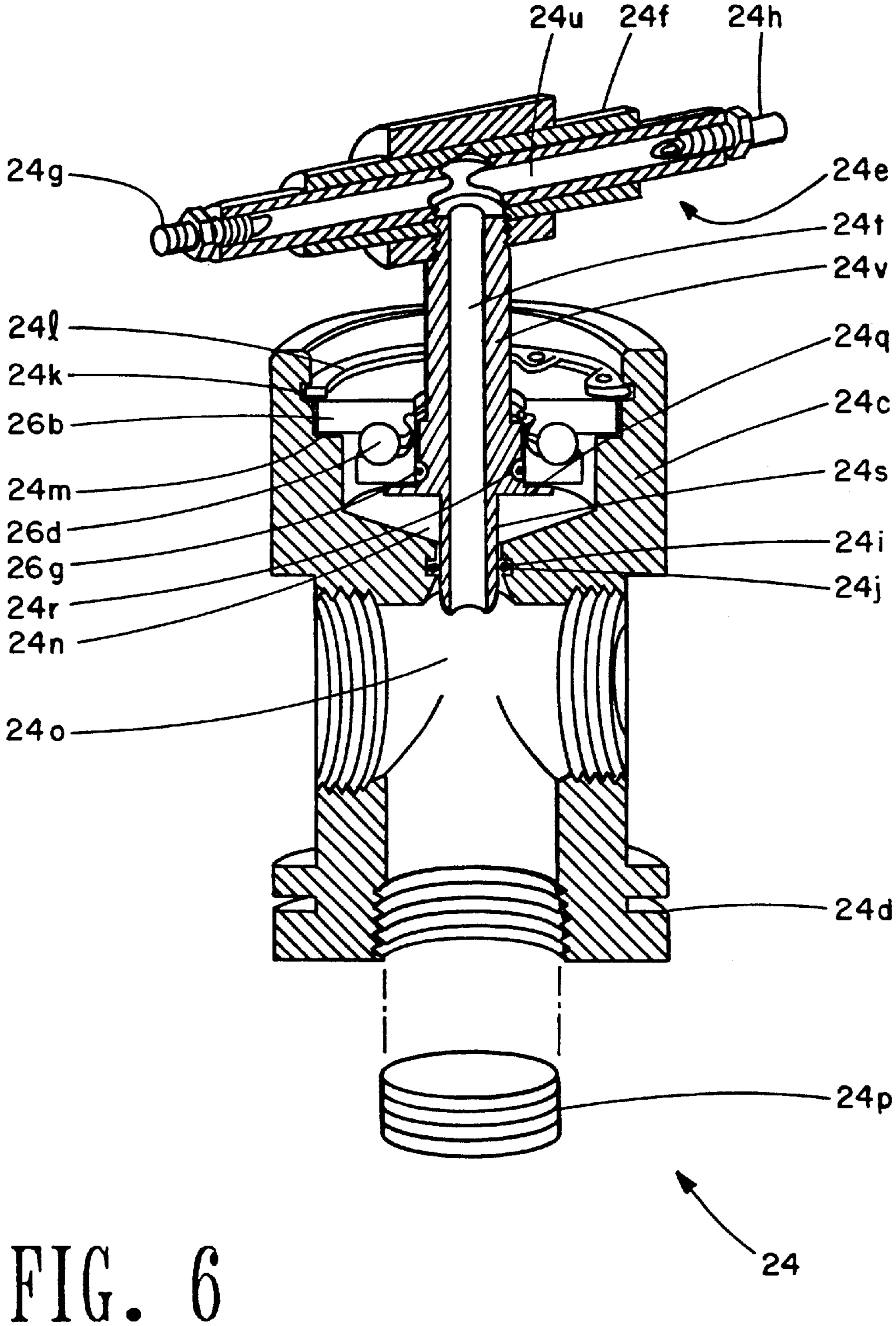
FIG. 6 is a sectional view of the rotary spray nozzle.
Figure 7:
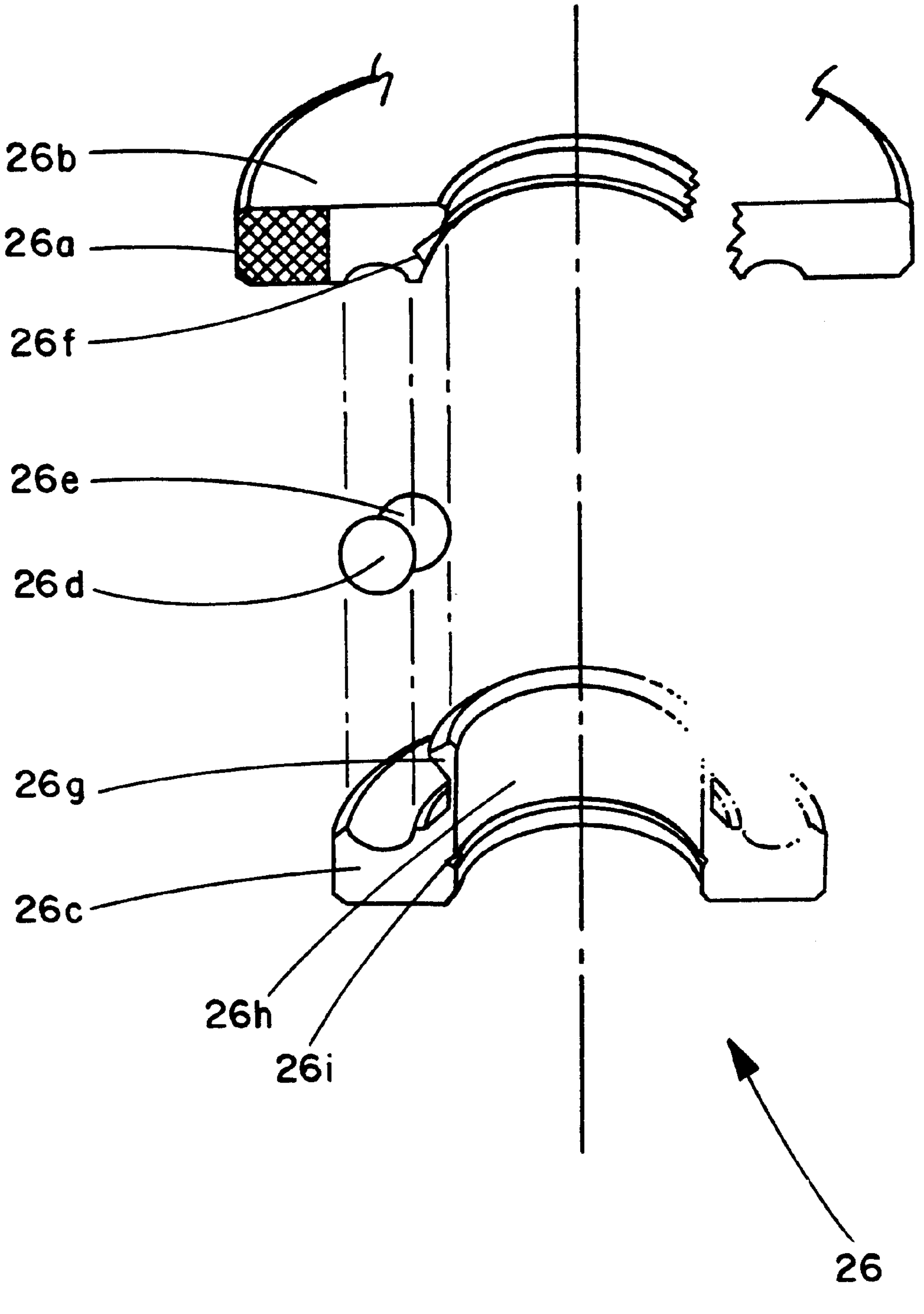
FIG. 7 is an exploded view of the bearing for the rotary spray nozzle.

The complete bio-mechanical system is generally comprised of eleven major interrelated (integral) components including: A. a bio-reactive fluid reclaim unit 200, FIG. 1, 2, and 3, B. a fluid collector/fan mount adaptor manifold 36, FIG. 4, C. a universal low volume/low pressure spray boom assembly 23, FIG. 1, D. low volume rotary spray nozzles 24, FIGS. 1, 4 and 6, utilizing E. self-centering thrust-bearing 26, FIGS. 6 and 7, F. mist-blocking baffle filter system 600, FIGS. 1, 8 and 9, G. universal hood gutter system 700, FIGS. 1 and 9, H. a fluid return sump assembly 28, FIGS. 1, 5 and 9, I. a makeup solution injector reservoir 40, FIGS. 1 and 9, J. a wash fluid return-piping system 32, FIGS. 1, 5 and 9, K. and a bioremediation fluid discharge line 38, FIG. 1.

Figure 2:
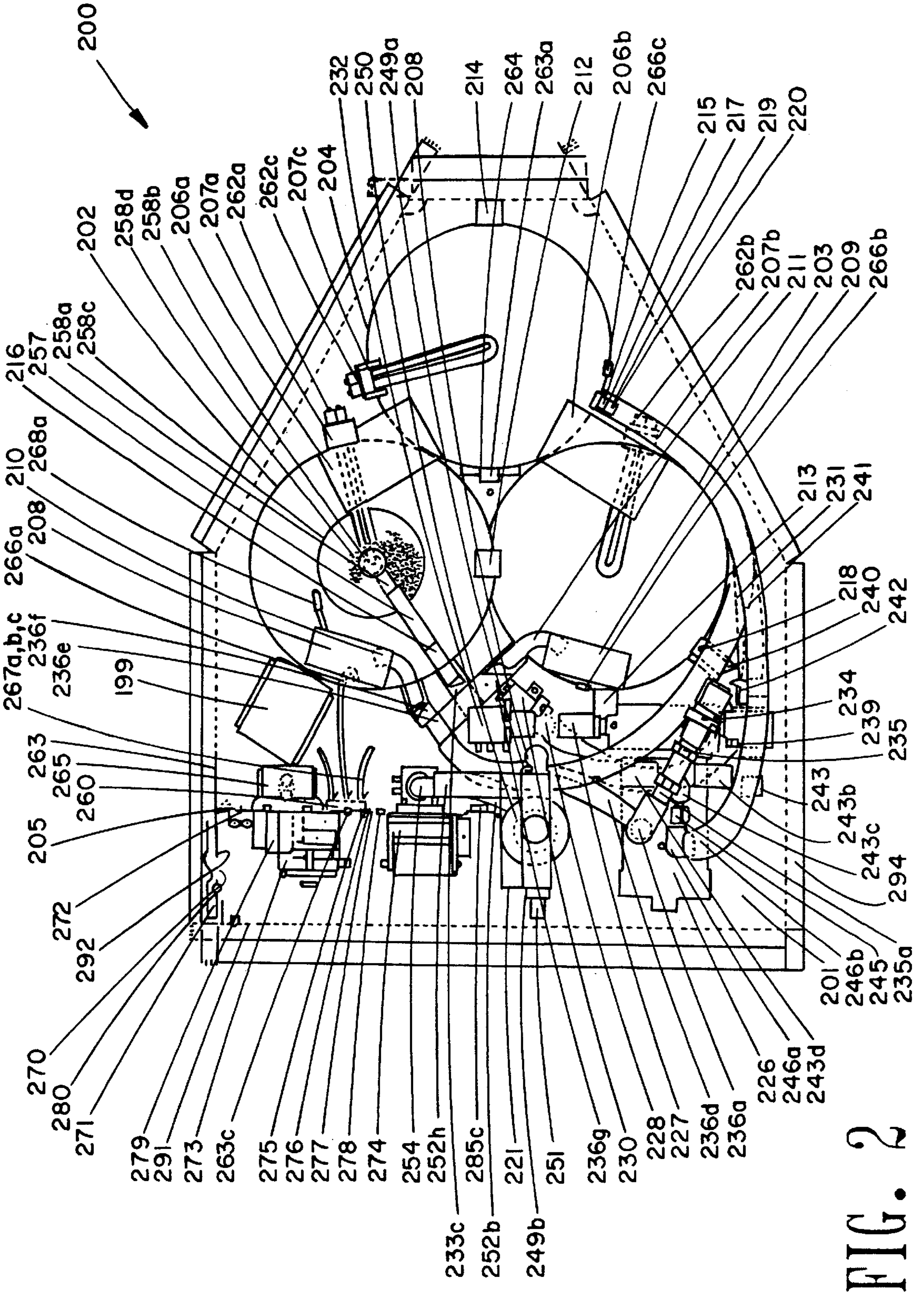
FIG. 2 is a top view of the bioremediation unit.
Figure 3:
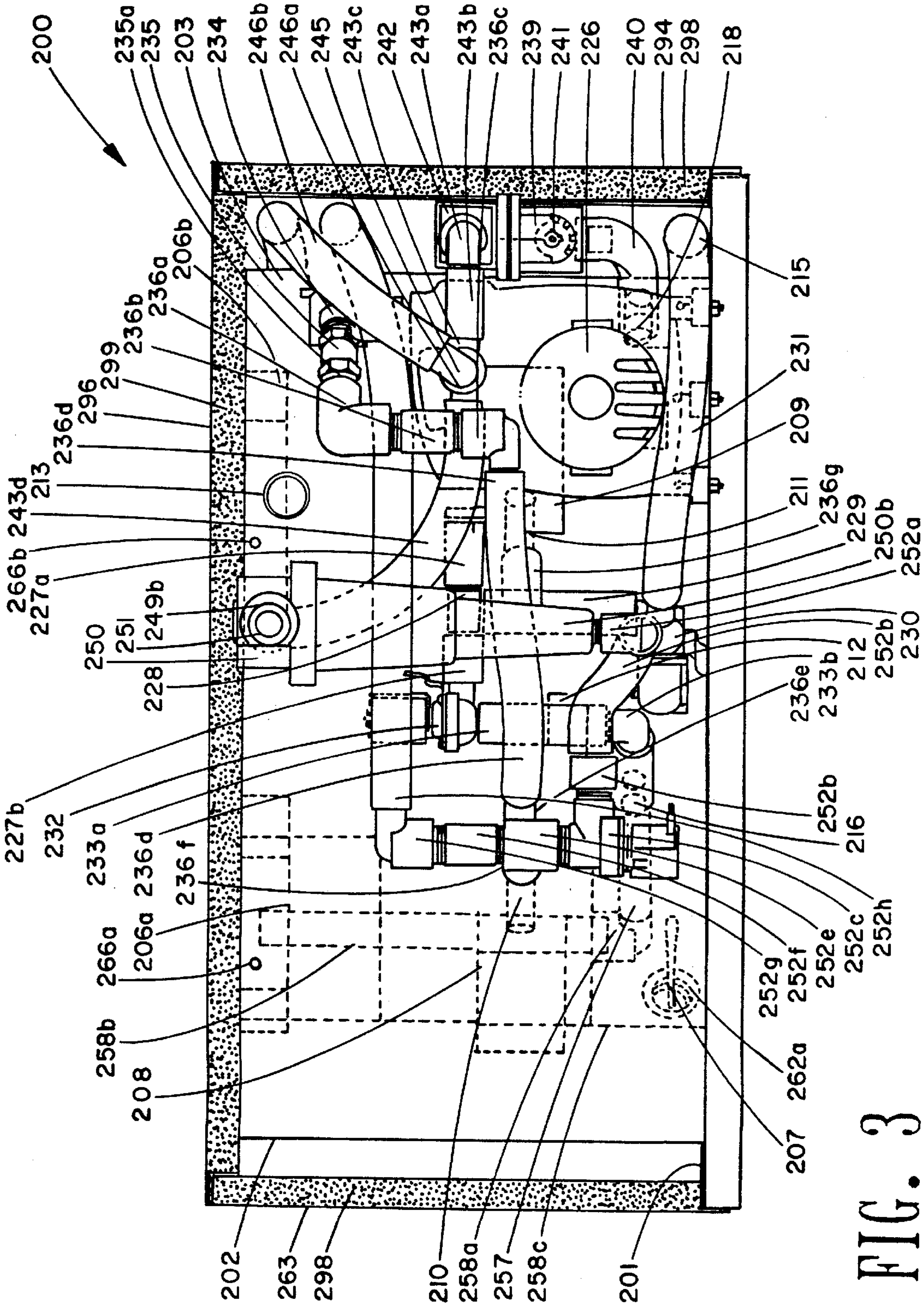
FIG. 3 is an elevational view of the bioremediation unit.

More specifically, bio-reactive fluid reclaim unit 200, as depicted in top view, FIG. 2 and end view FIG. 3 (electric control box omitted from FIG. 3 for clarity) is comprised of:

A common base plate 201 which serves as a mounting surface for circulation chamber or tank 202, receiver chamber or tank 203, discharge chamber or tank 204, electrical component control box 205, the main system pressure pump 226, fluid reclaim cycle suction solenoid valve 230, optional heat kit fan unit 199, and the primary common support and bottom attachment point for side cover panels 291, 292, 293, and 294.

Circulation tank or chamber 202 is fitted with fluid equalization port 212 common to receiver tank 203. Circulating tank 202 is also fitted with a first directional fluid flow discharge fitting 210, centrifuge fluid flow stratifier 208, cleaning cycle suction port 216, grease transfer wier or channel 206*a* common to discharge tank 204, a heat element receptacle 207*a*, a heat element 262*a* (to prevent freezing), and an air line inlet port (grommet) 266*a*.

Receiver tank or chamber 203 is likewise fitted with fluid equalization port 212 common to Circulation tank 202, the main system inlet port 213, a second directional fluid flow discharge fitting 211, centrifuge fluid flow stratifier 209, timed equalization port 218, grease transfer weir 206*b* common to discharge tank 204, a heat element receptacle 207*b*, a heat element 262*b*, and an air line inlet port (grommet) 266*b*.

Discharge tank or chamber 204 is fitted with 2 grease transfer weirs 206*a* and 206*b* common to tanks 202 and 203 respectively, fluid reclaim cycle suction port 215, timed equalization port 217, fluid agitation inlet port 219, spin-down filter sediment discharge port 220, a heat element receptacle 207*c*, a heat element 262*c*, a thermostat mounting bracket 264, an airline inlet port (grommet) 266*c*, and the main system bio-remediation fluid discharge port 214.

Electrical component control box 205 is configured to accept wiring grommets 275, 276, 277, 278, and 280 respectively to facilitate installation of heat element, solenoid valve, pressure pump, air pump, and low voltage contactor wiring. Control box 205 internally houses control wiring distribution terminal block 272, a 24 hr. timer 273, a sub-process timer 274, and optional "fan kit" component/low-voltage transformer 279, heat element contactor 263*c* and optional heat kit fan contactor 285*b*. The exterior of control box 205 serves as a mounting surface for air-pump 265, air valve manifold 269, sediment discharge solenoid valve 254, wafer bi-metal snap disk thermostat 285*c* to control optional heat kit 285, spin down filter mounting bracket 221, main power inlet 270, and corresponding main power disconnect 271.

Other components in bio-reactive fluid reclaim unit 200 include those relative to fluid flow beginning with primary suction line 227*a* connecting main system pump 226 by way of vertical fluid reclaim cycle suction line "T" 228 to two separate fluid reservoirs, tank 202 and tank 204. Vertical fluid reclaim cycle suction line 229 connects fluid reclaim cycle suction solenoid control valve 230 to fluid reclaim cycle suction line 231 which terminates at tank 204 fluid reclaim cycle suction port 215.

Secondary suction line 227 connects suction line "T" 228 to cleaning cycle suction solenoid control valve 232 which transitions vertically to cleaning cycle suction line assembly 233*a, b* and *c*, terminating at tank 202, cleaning cycle suction port 216, which extends within tank 202 by way of suction strainer tube 257 to ultimately connect the cleaning cycle suction line to a bleed filtration system assembly 258 located in the center of circulation tank 202, comprised of a suction strainer center tube receptacle 258*a*, a perforated stainless steel suction strainer center tube 258*b*, extending vertically in the center area of a mesh suction strainer filter housing 258*c* containing bulk polyester fiber filter media 258*d*.

Pressure and flow developed by main system pump 226 is produced through two separate ports. The first, located on the top of main system pump 226, is fitted with fluid reclaim cycle pressure solenoid valve 234 which connects to fluid reclaim cycle flow valve 235. A ¾" nipple 235*a* connects flow valve 235 to fluid reclaim cycle pressure line assembly 236 which is comprised of a 90° FNPT "L" 236*a*, a short pipe nipple in the vertical position 236*b*, a FNPT HB INSERT 90° "L" 236*c*, a preformed hose 236*d*, a hose insert "T" 236*e*, and termination hose 236*f* terminating in connection to first directional fluid flow discharge fitting 210, and termination hose 236*g* terminating in connection to second directional fluid flow discharge fitting 211.

The second and main pressure port is located on the side of main system pump 226 opposite the suction port and is fitted with cleaning cycle pressure solenoid control valve 242 which connects to cleaning cycle internal pressure line assembly 243 comprised of FNPT/Insert 90° "L" 243*a* first internal pressure hose 243*b*, fluid agitation insert "T" 243*c* (see next par), second internal pressure hose 243*d*, which connects to 90° spin down filter intake fitting 208 which, in passing through spin down filter mounting grommet 249*a*, both supports and pressurizes spin down filter 250 at its inlet. Straight spin-down filter discharge fitting 251 passing through spin-down filter mounting grommet 249*b* supports the spin-down filter at its discharge side and connects to and pressurizes exterior pressure line 21 (FIGS. 1 and 4) which passes through a grommet at the top of right side back cover 294 and out of the unit to pressurize the spray boom assembly 23.

Fluid agitation insert "T" 243-C diverts excess pressure from cleaning cycle internal pressure line assembly 243 through fluid agitation flow valve 245 (approximately 4 gpm), which connects to fluid agitation pressure line assembly 246 comprised of MNPT insert 90° "L" 246*a* and fluid agitation hose 246*b*, terminating with attachment to fluid agitation inlet port 219 and a fan spray nozzle (not shown) in tank 204. A perforated plate (not shown) with one-sixteenth inch diameter holes may be placed mid-level and horizontaly across tank 204 to bi-sect tank 204 such that only the region above the perforated plate will be subjected to the agitation or turbulence caused by the fan spray.

The time-controlled equalization of fluid levels between common tanks 202, 203, and discharge chamber tank 204 is achieved by connecting fluid equalization line 241 to equalization port 217 on the one end and fluid equalization solenoid control valve 239 on the other, then connecting solenoid control valve 239 to timed equalization port 218, utilizing fluid equalization line 240.

Sediment is flushed automatically from spin-down filter 250 by way of spin-down filter sediment flush assembly 252 comprised of spin-down filter sediment flush fitting 252*a* which is a 90° FNPT/insert fitting attached to the bottom discharge port of the spin-down filter sediment bowl 250*b*, facilitating the connection of primary sediment flush line 252*b*, which connects to sediment flush solenoid control valve 252*c*. Sediment is then carried in flow under pressure upward through sediment flush control valve riser-subassembly 252*d*, comprised of a FNPT coupling 252*e*, a short pipe nipple 252-*f*, and a FNPT/insert 90° "L" fitting 252*g*, which connects to secondary sediment flush line 252*h*, which terminates in connection with spin-down filter sediment flush discharge port 220 in tank 204.

Compressed air is generated internally by air pump 265 and is injected into each of the three tanks 202, 203, 204. Air pump 265 is connected to air valve manifold 269. It then passes through air line 267*a* to Tank 202. Air line 267*b* to Tank 203 and air line 267*c* to Tank 204 where it is disbursed in the fluid by submerged air stones 268*a, b* and *c* (*b* and *c* not shown).

The bio-reactive/fluid reclaim unit 200 is fully housed (enclosed) by outer cabinet assembly 290, comprised of electrical component control box front cover 291, electrical component control box left side cover 292, left side/front cover 263, right side back cover 294, and top cover 296. All side covers are insulated against temperature extremes with ¾" styrofoam HDIB (high density insulation board) 298 laminated to the inside surfaces. The top cover supports 1" styrofoam HDIB 299 laminated to its inside surface which in addition to its insulation properties provides a common top seal for tanks 202, 203, and 204 by compression seal of the inner surface of the HDIB to the top rim of the tanks when fully assembled and secured in place.

Electrical component control box 205 being slightly taller than tanks 202, 203, and 204 interfaces with and projects into a corresponding groove in the top cover HDIB inner surface to provide a natural seal against water being introduced into the electrical component control box resulting from inadvertent movement of the unit or failure of certain internal pressure system components.

One inch styrofoam HDIB 299 is laminated to the under side of system base plate 201 and, in addition to its insulation properties, provides a suitable surface to be placed in contact with roofing surfaces 1, evenly distributing the full operating weight of unit 200 over the entire bottom area, eliminating the need for roof penetrations, mounting frames, etc., for most rooftop installations.

The outer cabinet assembly is attached and secured by a combination of interlocking sheet metal connections and PEM fasteners (pressed in place nuts) 300 in a manner easily understandable by those skilled in the art.

Figure 4:
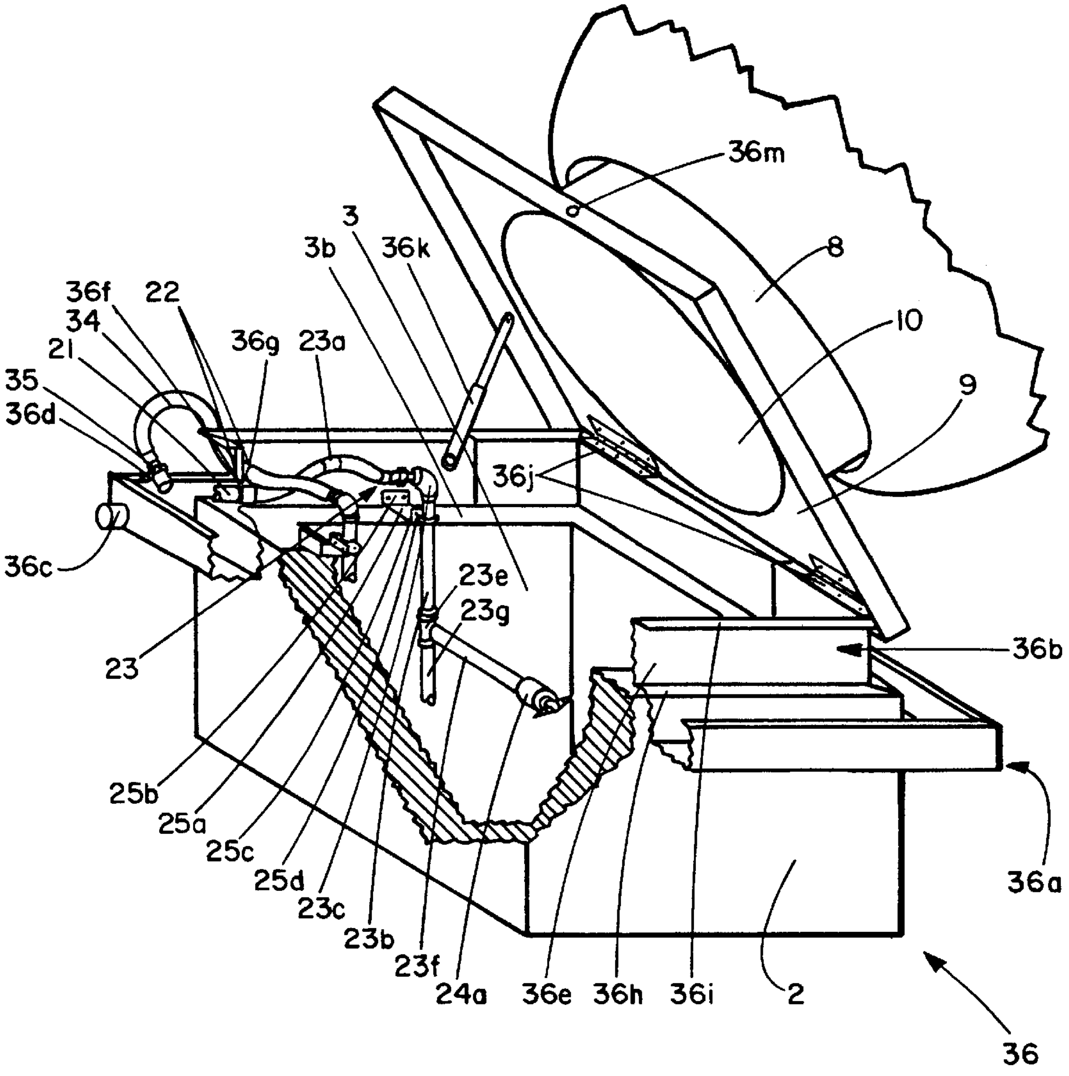
FIG. 4 is a perspective view of the fluid collector/fan mount adaptor.

Referring to FIG. 4, fluid collector/fan mount adapter 36 includes, in its unitary section modulous, two distinct shapes, each functionally independent of the other and although joined are referred to separately herein as fluid collector 36*a* and fan mount riser adapter flange 36*b*. Fluid collector 36*a* receives fluid from flush nozzle 35. Flush nozzle 35 receives fluid from return pipe 32. Fluid collector flush nozzle mounting bracket 36*d* provides a means for rigid attachment of fluid collector flush nozzle 35 at the overall end of and in a downward angle over and directionally in line with the center flow line of fluid collector 36*a*. Said configuration results in the recirculating washing solution being discharged under pressure by fluid collector flush nozzle 35 during daily cleaning cycles being directed into the center flow line of fluid collector 36*a* where it flows in a forced counter clockwise rotation throughout fluid collector 36*a*, thereby emulsifying, collecting, and transporting daily oil and grease accumulations (grease inside exhaust fan 8 and mounting base 9 will seep down and collect in fluid collector 36*a*) to bio-reactive/fluid reclaim unit 200 by way of collector drain neck 36*c*, which provides the means for the attachment of fluid collector drain line 37, ultimately directing fluid from collector 36*a* to bio-reactive fluid reclaim unit 200.

Integral fan mount riser adapter flange 36*b* provides a 6" vertical extension wall 36*e* of the exhaust fan 8 mounting base 9. This feature facilitates the introduction of spray boom supply line 21 and fluid return line 34 through grommet or bulkhead fitting S22 installed in spray boom supply port 36*f* and fluid return port 36*g*, eliminating any need for penetrating the flue 3 or exhaust fan 8 components.

Fluid collector/fan mount adapter 36 is constructed of heavy gauge aluminum sheet, providing the rigidity to support moderate to heavy compressive loads when formed. Horizontal mounting leg 36*h* provides sufficient surface area to bear on the top outside rim of exhaust flue structures 3*b* and is intended to be permanently attached, utilizing a continuous generous bead of urethane adhesive/sealant, again eliminating penetrations in flue components. Standard sheet metal overlapping joints are utilized in the assembly of fluid collector/fan mount adapter 36; however, tolerances between components, when assembled, is considerable to allow ample free void area for a continuous bed of urethane adhesive sealant utilized both to permanently bond the components and provide a liquid tight sealed condition without soldering, welding, or utilizing penetrating fasteners.

The horizontal fan mount flange 36*i*, projects outward at a 90° angle from fan mount riser 36*e* to provide a bearing surface for the exhaust fan base 9. However, the overall projection of 36*i* is ⅛" less than the inside overall bearing surface of horizontal mounting leg 36*h*, assuring an acceptable overall finished dimension slightly smaller than that of the exhaust flue housing 2 that previously supported exhaust fan base 9. This condition provides the added clearance necessary to facilitate the re-installation of exhaust fan 8 in a hinged connection with top horizontal fan mount flange 36*i*. This is accomplished by utilizing one pair of strip hinges, 36-J, permanently attached to each end of horizontal fan mount flange 36*i* (welded) and subsequently bonded to the underside of exhaust fan base 9, utilizing a full bed of urethane adhesive/sealant over the entire surface of each hinge leaf and two 8 machine screws, nuts and washers with each hinge.

Hinging the exhaust fan allows servicing of the interior of the exhaust flue 3 and related components and the underside of the exhaust fan 10 without totally removing and handling the full weight of the exhaust fan unit 8.

Exhaust fan unit 8 is mechanically supported in the up or open position by a sliding fan support stay 36*k* attached to the top of the exhaust flue 3*b* at the one end and the underside of the exhaust fan base 9 at the other end, utilizing two stainless steel self-drilling screws at the exhaust flue 3*b* connection and two machine screws, nuts, and washers at the base 9 connection.

The exhaust fan 8 is secured in the down/operating position by an exhaust fan spring latch mechanism 36*l* attached to the underside of top horizontal fan mount flange 36*l* opposite the hinged side with the vertical downward flange of the exhaust fan base 9 bored to interface with 36*l* as exhaust fan spring latch strike hole 36*m*.

Figure 1:
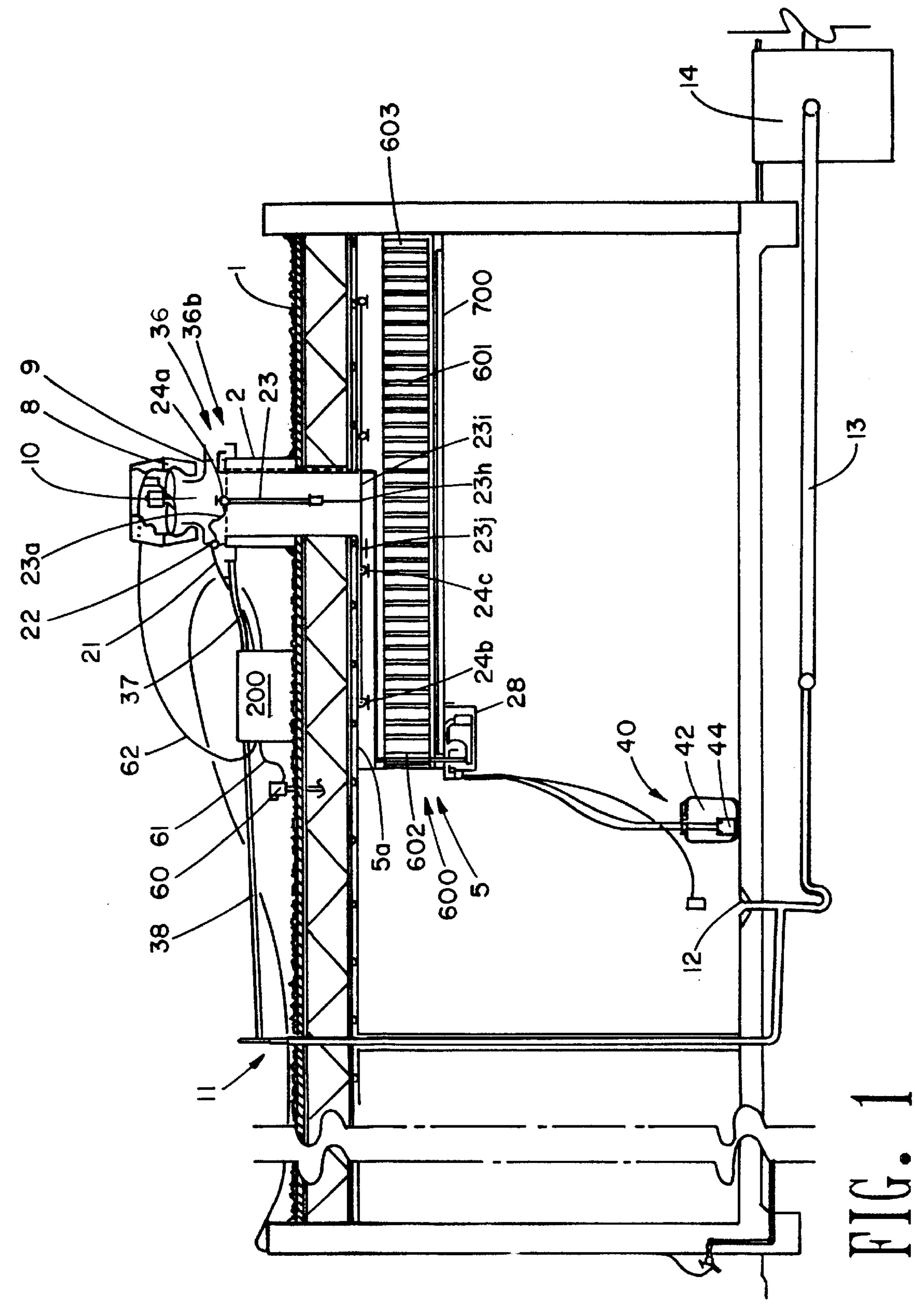
FIG. 1 is an elevational view of the system incorporating the present invention.

Low volume spray boom assembly 23, FIG. 1 and 4, is comprised of an SS braided pressure hose 23*a*, which connects one end to spray boom supply line 21 at bulkhead fitting 22 integral with fan mount riser 36*e*, and the other end to FNPT 90° "L" 23*c* which transitions the pressure hose to connect vertically with first boom section 23*b* which is the uppermost short section of pipe (galvanized steel) (length varies 6– to 18") in spray boom assembly 23. The vertical and center horizontal sections of spray boom assembly 23 are suspended within the exhaust flue 3 by spray boom top support bracket 25*a*, which is comprised of a stainless steel clip 25*a* field-formed on one end, 25*b*, to a 90° angle to be attached to fan mount riser 36*e* utilizing SS self-drilling screws, leaving sufficient horizontal length (length varies) to allow the clamp end, 25*c* of 25*a* to extend slightly over the inside edge of the top inside vertical surface of exhaust flue 3. The pipe clamp 25*d* encircles and secures spray boom section 23*b* in the vertical position.

First vertical spray boom section 23*b*, having a length not greater than twenty four inches (length varies) from the underside of exhaust fan unit 10 extending downward connects to galvanized "T" 23*e* facilitating the installation of a short galvanized nipple 23*f* which mounts and pressurizes rotary spray nozzle 24*a*. An additional three foot section of galvanized pipe for second spray boom section 23*g* extends downward from "T" 23*e* and in flues five foot or less will transition directly into the horizontal spray boom 23*i* with connection to horizontal spray boom "T" 23*h*, FIG. 1. In the case of long vertical flues, additional "T" 23*e*, nipples 23*f*, and spray nozzle 24*a* assemblies may be connected to extend the vertical boom sections 23*b* and *g* as required with spacing of rotary spray nozzles 24 preferrably not exceeding three feet.

First horizontal spray boom sections 23*i* and *j*, (FIG. 1), are galvanized pipe sections connected to horizontal spray boom "T" 23*h* extending in either or opposite directions to connect to and be supported by rotary spray nozzle 24*b*, (FIG. 1). Rotary spray nozzle 24*b* interlocks with a short stainless steel clip and spray nozzle mounting bracket (not shown buy similar to clip 25*a*, FIG. 4) which attaches to the inner top surface 5*a* of the exhaust hood 5, FIG. 1, and interlocks with an outside snap ring groove 24*d* in rotary spray nozzle housings 24*b* and 24*c* (24*b* not shown). Rotary spray nozzle 24*b*, having one side hole, is installed at the termination of the horizontal spray boom and serves as an end cap and boom support in addition to being a nozzle. Rotary spray nozzle 24*c*, having two side holes, is also utilized as a boom coupling and hanging device.

The design of the spray nozzle housing 24*b* and 24*c* when interlocked with spray nozzle mounting bracket (not shown) holds the horizontal spray boom in place both vertically and laterally. The longitudinal axis of the boom assembly is then secured by two cotter pins (not shown) installed in each end of bracket (not shown) on either side of the nozzles. Spray nozzle mounting bracket is attached to the inner surface of the exhaust hood 5, utilizing one #8 stainless steel self-drilling screw (not shown) in the center of each bracket.

Low volume rotary spray nozzles 24, appear in three configurations 24*a*, 24*b* and 24*c* (24*c* shown in FIG. 6), each having a functionally unique nozzle housing constructed of machined or molded NORYL plastic, a free machining, non-flammable synthetic compound produced by G.E. Plastics Division. Nozzle housing 24*a* exhibits one hole threaded FNPT in one end and no outside snap-ring groove. Nozzle Housing 24*b* also exhibits a FNPT threaded hole in one end and one additional side hole along with an outside snap-ring groove 24*d* at one end. Nozzle housing 24*c* exhibits three FNPT holes, one in the end and two additional holes, one in each side, and the same outside snap-ring groove 24*d* at one end. The outside snap-ring groove 24*d* is intended to interface with spray nozzle mounting bracket (not shown) and support the low volume spray boom assembly 23 (see previous section). Otherwise, all features of the three nozzles are identical. Nozzles 24 commonly exhibit a rotor (stainless steel) 24*e*, a rotor arm (aluminum) 24*f*, low volume spray emitters—2 each, 24*g* and 24*h*, an o-ring gland 24*i* and an o-ring 24*j*, an ID snap ring groove 24*k* and an ID snap ring 24*l*, a self-centering, thrust-bearing 26, a bearing seat 24*m*, and thrust bearing chamber 24*n*, a fluid chamber 240, and in the case of nozzles 24*b* and 24*c*, a MNPT plug 24*p* which seals the end hole subsequent to assembly and insertion of O-ring 24*j* in O-ring gland 24*i*. However, the end holes and MNPT plugs in nozzle housings 24*b* and 24*c* are optional and intended only to facilitate the ease of installation of O-ring 24j, and may be eliminated as a design feature if desired.

In assembly, rotor 24*e* is pressed into the center bore of self-centering, thrust-bearing 26 and bears compressive loading under pressure by rotor bearing seat flange, 24*q* being seated against thrust-bearing 26. Accidental disassembly of rotor 24*e* from thrust-bearing 26 is avoided by mating thrust-bearing detent 24*r* with rotor detent 26*g*. Rotor 24*e* in assembly with thrust-bearing 26 is inserted in rotor housing 24 with rotor tail shaft 24*s* extending into fluid chamber 24O by passing through O-ring 24*j* previously inserted in O-ring gland 24*i*. O-ring 24*j* seals thrust-bearing chamber 24*n* separate from fluid chamber 24*o* with minimal restriction to the friction-free rotation of rotor 24*e* provided by thrust-bearing 26. The rotor 24*e* thrust-bearing 26 assembly is held over its center rotational axis by the inherent design of self-centering, thrust-bearing 26, shown in FIG. 7. The larger diameter self-centering flange 26*a* of thrust bearing 26, top race 26*b*, is seated in nozzle housing thrust bearing seat 24*m* and retained against pressure by snap ring 24*l* inserted in snap ring groove 24*k*. The close tolerances of thrust-bearing seat 24*m* relative to thrust bearing, self-centering flange 26*a* horizontally and snap-ring 24*l* vertically assure a securely centered rotor assembly, minimizing any tendency to bind, resulting in friction-free rotation.

Rotor arm 24*f* is attached at its center by threaded connection perpendicular to rotor stem 24*v* and provides the means for extending the rotor fluid canal 24*t* carrying fluid under pressure from fluid pressure chamber 24*o* through rotor arm fluid canal 24*u* to low volume spray emitters 24*g* and 24*h* installed in each end of rotor arm 24*f* by threaded connection and reactively transfers the light thrust energy produced by the volume spray emitters 24*g* and 24*h* in operation under pressure back to rotor 24*e* which provides the motive force that achieves reactive rotation.

The low volume rotary spray nozzles 24 are easily reconfigured to provide high or low volumes of fluid in a wide array of spray patterns by simply changing the spray emitters 24*g* (right angle, 180 degree, low-volume emitters such as commonly used in drip irrigation may be used) and 24*h* to produce the desired result. The overall size of rotary spray nozzles 24 may be altered to any desired dimension as required. Operating pressure is virtually unrestricted from less than 5 PSI up to 100 PSI and above, depending on materials used to construct the various nozzle components. As configured, low volume rotary spray nozzle 24 produces a totally diffused, non-directional spherical spray pattern, providing complete coverage in both the vertical and horizontal plane, at a very low volume of less than 0.4 gallons per minute at design operating pressure ranges between 20 and 40 PSI. It is easily understandable that a low volume of washing solution being evenly sprayed in close proximity with all interior vent hood surfaces under pressure to obtain full coverage will mildly impinge upon these surfaces and remove daily accumulations of oily residue from cooking, without copious amounts of solution flooding the interior of the vent hood 5.

Self-centering, thrust- bearing 26 is comprised of four primary components, including self-centering top race 26*b* and interlocking bottom race 26*c*, which are machined or molded of DELRIN, a free machining synthetic material exhibiting good dimensional stability and low moisture absorbency, DELRIN ball bearings 26*d* and glass ball bearings 26*e*. Top race 26*b* defines female interlocking detent 26*f* in its bore to interface with male interlocking detent 26*g*, on O.D. profile of bottom race 26*c* which, when engaged with 26*f*, unitizes the two races to cage and retain ball bearings 26*d* and 26*e*. Minimum but adequate clearance in the detent area minimizes frictional resistance between the races in rotation, particularly under loaded conditions. Increase in load compresses the two races slightly which increases the clearance in the detent area, transferring one hundred percent of the load, friction free, to the bearings 26*d* and *e*. Glass ball bearings 26*e*, which may also be stainless steel or other material, resist compression and hold their shape. However, glass will abrade itself, therefore, DELRIN ball bearings 26*d* are utilized alternately to isolate glass bearings 26*e*, further minimizing friction.

Self-centering top race 26*b* exhibits an outside diameter larger than the outside diameter of bottom race 26*c*. This extension of top race 26*b* is referred to as an integral top race self-centering flange 26*a* and serves to center thrust-bearing 26 and whatever shaft or component (rotor stem 24*v* shown in FIG. 6) which may be co-axial with its rotational axis or integral to its bore 26*h* (FIG. 7) when mounted in a comparable fixture (nozzle housing 24*c* shown) having an inside diameter only several thousandths larger to accommodate top race self-centering flange 26*a*. Thrust bearing bore 26*h* may be threaded or, as with top race 26*b*, may be detailed with an integral shaft female detent referred to here as rotor detent 26*i* to facilitate the installation of rotor 24*e*, providing an interface with a thrust-bearing detent 24*r*.

In as much as self-centering, thrust-bearing 26 is self-centering, a mounting fixture for shafted components, and a unitized thrust bearing, it eliminates the need for the more conventional type of assemblies where shafts are supported rotationally by ball, roller, needle bearings or bushings, longitudinally by pins, nuts, keepers, etc., and thrust bearings usually centered between thrust washers to reduce longitudinal compressive friction loads.

Figure 8:
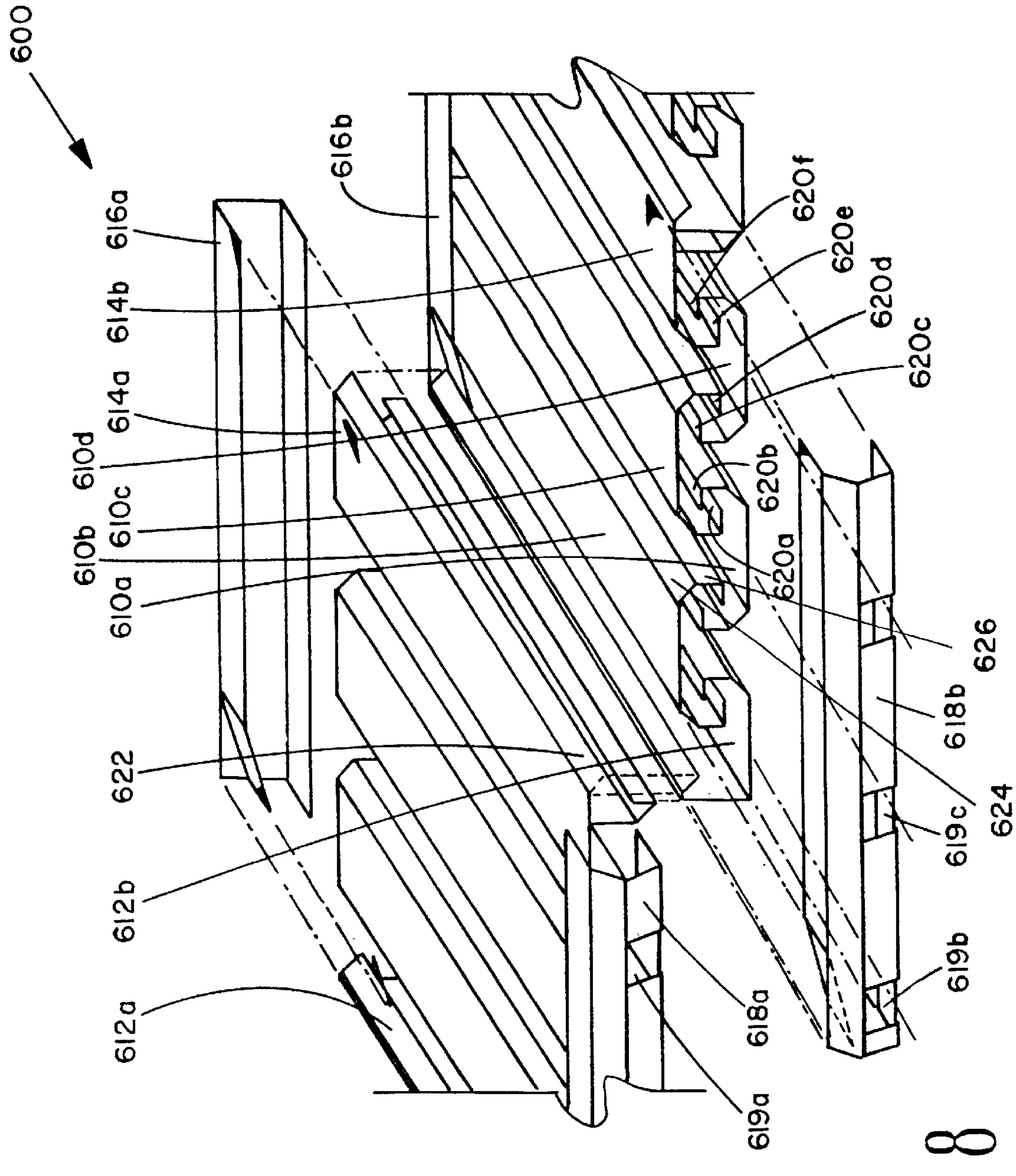
FIG. 8 is an exploded view of the baffle filter system.
Figure 9:
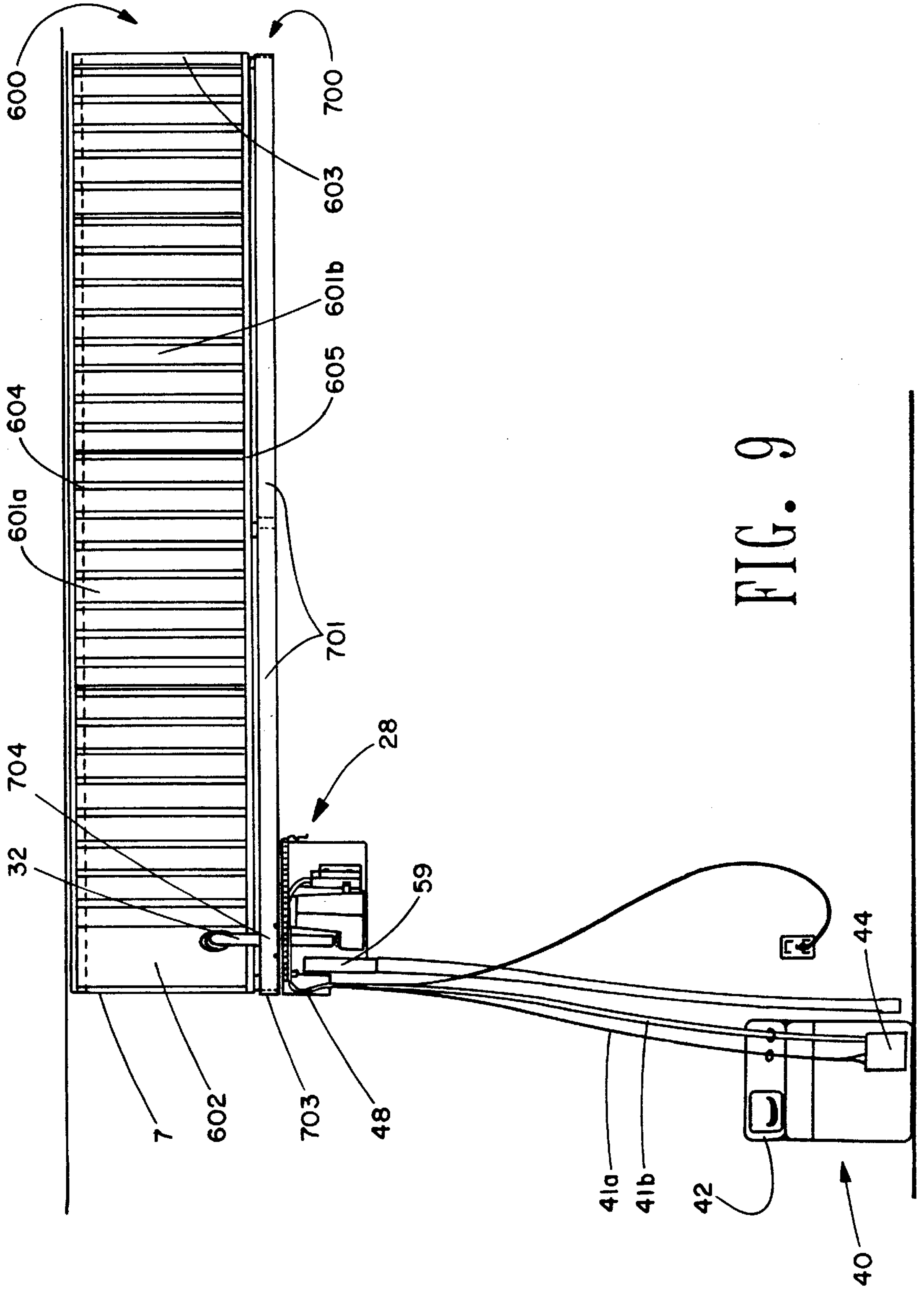
FIG. 9 is an elevational view of vent hood, fluid return sump assembly and make up solution injector reservoir.

Universal retrofit mist-blocking baffle filter system 600, FIGS. 1, 8 and 9 are comprised of baffle filter units 601, header block 602, termination block 603, top splash guard 604, and bottom splash guard 605 all produced in various sizes to achieve universality in retrofit applications with any existing standard exhaust hoods.

Baffle filter unit 601 comprises five components in its assembly; intermediate channel sections 610 (*a–d* referenced), male side channel 612 (*a* and *b* shown), female side channel 614 (*a* and *b* shown), top channel stringer 616 (*a* and *b* shown) and bottom channel stringer 618 (*a* and *b* shown).

Top channel stringers 616 and bottom channel stringers 618 are identical with the exception that bottom channel stringers 618 are perforated or have openings 619 (*a–c* referenced) to facilitate fluid drainage during the washing cycle. Top channel stringers 616 and bottom channel stringers 618 are attached in parallel to male side channel 612 and female side channel 614 at opposite ends. They form the outer frame of baffle filter unit 601. Intermediate channel sections 610 are arranged in an evenly spaced, interlocking configuration along and perpendicular to top 616 and bottom channel stringers 618 between and parallel to male and female side channels 612 and 614. The horizontal return legs 620 (*a–f* referenced) common to male and female side channels 612 and 614 and intermediate channel 610 are oriented in assembly in pairs overlapping, opposed and spaced from each other (e.g. in relation to each other return leg 620*a* and return leg 620*b* are overlapping, opposed and spaced from each other) to provide the means for blocking the transmission of airborne washing solution into the kitchen environment. Each return leg 620 lies in a plane which is approximately parallel to the plane which contains the respective intermediate channel section 610. Two angled walls 624, 626 create the transition from intermediate section 610 to return leg 620. The complete "S" track achieved by the overlapping, opposed and spaced interlocking horizontal return legs 620 adequately contains any splatter or spray resulting from or during the washing cycle within the confines of the exhaust hood 5 duct area while providing a tortuous air path for exhaust air flow with minimal static restriction. The design of male and female side channels 612 and 614 in modular sections incorporates an overlapping flange 622 with male side channel 612 which, when coupled in place parallel to female side channel 614 of the next baffle filter unit 601*b*, provides a flashed connection between baffle filter units 601 *a* and *b* installed in series to further prevent the passage of spray or splashed washing solution beyond the baffle filter units 601.

During operation of the exhaust hood, the baffle filter system 600 will collect grease as the air entrained with grease is pulled through the baffle filter system 600. The exhaust will be "off" when it is time to spray and clean the exhaust hood 4. Ordinary baffle filter systems (not shown) allow spray wash to deflect through the filter system. However, in the present invention, the paired overlapping, opposed and spaced return legs 620 will not allow spray wash to deflect through the baffle filter system 600 regardless of the angle of impingement of the spray (i.e. it will contain the washing fluid).

Universal hood gutter system 700, FIGS. 1 and 9, is designed to collect the washing fluid that drains out of the exhaust hood 5 via draining down the baffle system 600 during the cleaning process. Most conventional exhaust hoods are equipped with an integral grease collection gutter which usually suffices for this purpose. However, in instances where the usual grease gutter is too shallow to handle the volume of the cleaning solution or other fault is found, universal hood gutter system 700 may be utilized in retrofit.

Universal hood gutter system 700, FIG. 9, may be of any length when assembled and is constructed of stainless steel members break-formed in three foot sections, joined by male/female overlapping connections considered standard in the sheet metal industry. These overlapping connections are intended to be joined and permanently sealed utilizing urethane adhesive sealant and pop rivets eliminating the need for welding, soldering, or penetrating fasteners. Horizontal flange 701 provides the means for attachment by interlocking with gutter system clip 702 which is permanently attached to the underside of exhaust hood 5 at three foot on center at each gutter lap connection. Gutter system 700 end blocks 703 close each end of the gutter system 700 and are permanently installed utilizing urethane adhesive to provide a liquid-tight connection. A large (two inch diameter) drain hole 704 is provided in one section of the gutter system 700 as a means for draining the washing fluid from the gutter system 700 into fluid return sump assembly 28.

Figure 5:
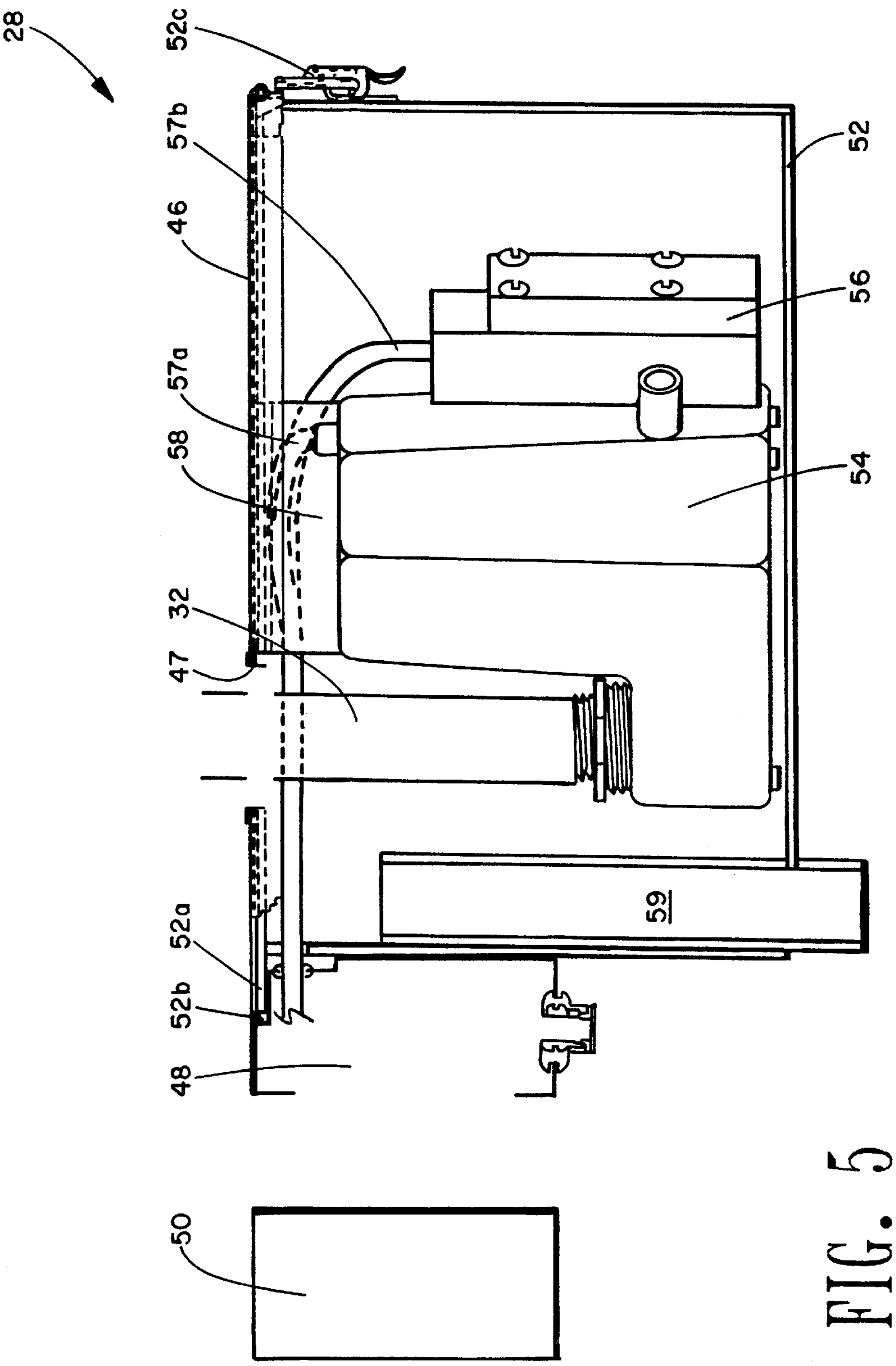
FIG. 5 is an elevational view of the fluid return sump assembly.

Fluid return sump assembly 28, as seen in FIGS. 1, 5 and 9 is attached to either end or the center of the exhaust hood grease gutter 7 or universal hood gutter system 700. It is comprised of return sump mounting plate 46, sump assembly control box 48, control box cover 50, sump box 52, sump pump 54, liquid switch 56, and sump pump spacer block 58. Return sump mounting plate 46 has a two inch diameter hole 47 which mates with a corresponding hole in the exhaust hood grease gutter 7 or universal hood gutter system 700 which facilitates drainage into the fluid return sump assembly 28. Sump pump 54 is top mounted in suspension below return sump mounting plate 46. Sump pump spacer block 58 provides the means for routing the pump and liquid switch power cords 57*a* and 57*b* respectively over the top of sump pump 54 for internal connection to the power supply within control box 48.

Sump box 52 is removably top-mounted to and in suspension below return sump mounting plate 46 at the one end by engaging sump box mounting flange 52*a* in a corresponding sump box mounting recess 52*b* perpendicular and along the top of control box 48 and at the other end by sump box draw catch 52*c*. The bottom of sump box 52 is positioned ⅛ inches below the overall bottom of sump pump 54. As liquid from the cleaning process collects in the sump box 52, liquid switch 56 automatically senses the moisture and energizes sump pump 54 which discharges the contents by way of primary return pipe 32. Fluid return sump assembly 28 also includes an overflow drain line 59.

To compensate for solution lost during the cleaning cycle to surface retention, evaporation and fluid degradation, make-up solution comprised of clean water, fresh oxidizer, and microbes is automatically injected into the system on a daily basis via make-up line 41. This solution is maintained in make-up solution injector reservoir 40, FIGS. 1 and 9, which comprises a polypropylene reservoir tank 42 and an injector pump 44. Injector pump 44 is activated during the timed cleaning by a one-shot delay timer located in sump assembly control box 48.

The system is designed to operate as follows: Referring to FIG. 1, the bio-remediation unit 200 located on the roof systematically supports integrated naturally passive and active mechanical processes which utilizes gravity and centrifuge to reclaim washing fluid for recirculation by allowing standing unagitated grease laden solution to separate by specific gravity. More specifically, during a 23-hour, 50-minute inactive period, oil and grease hydrolyzed into highly diluted molecular suspension resultant of the cleaning process, and being of lower specific gravity than water, separates and rises to the surface of the tanks 202, 203 and 204. The underlying remediated water can then be isolated and reused.

At the beginning of the cleaning cycle, a 24-hour timer energizes a subprocess timer having six separate cam actuated contacts, the first of which energizes and opens a normally closed low voltage contactor disabling the exhaust fan 8. The second contact closes 30 seconds later energizing a pressure pump 226 within the unit which is connected to two separate sources of suction, controlled independently by solenoid valves 230, 234. The first cycle has a duration of approximately 15 seconds and is referred to as the fluid reclaim cycle. A solenoid valve 230 located in a suction line connected to the lower portion of the discharge chamber 204 opens. The fluid from the lower strata of the discharge chamber 204 is then pumped under pressure to be discharged horizontally and parallel or tangential to the sides of both the receiver 203 and circulation 202 chambers which communicate commonly. The discharge chamber 24 is connected with the receiver 203 by way of an equalization line 241. However, during the fluid reclaim cycle, the equalization line 241 is closed by a solenoid valve 239 isolating the discharge chamber 204, as the sole source of supply for said fluid reclaim cycle. Fluid flow is stratified and directed to the center or mid level of the tanks by short horizontal channel sections 208, 209 to eliminate disturbance of the heavier solids settled at the bottom of the tanks 202, 203 and likewise allows the oil and grease to remain undisturbed at the top of the tanks. In this mode, the level of the discharge chamber 204 is lowered and the levels of the receiver and circulation chambers 202, 203 rise in a circular rotation. This rotation effects centrifuge to purge lighter solids out of suspension. Additionally, wier channels 206*a*, 206*b* at the top of both the receiver 203 and circulation chambers 202 communicate commonly with the discharge chamber 204. The lip of the openings to wier channels 206*a*, 206*b* are perpendicular to the direction of the rotating fluid providing a means for controlled discharge of the lower gravity oil and grease isolated at the top of the solution once the level in the receiver and circulation tanks 202, 203 sufficiently raises the oil and grease to be force spilled over into and trapped in the discharge chamber 204 to remain isolated there during the subsequent cleaning cycle. The fluid contained in the receiver and circulating chambers 202, 203 is thereby reclaimed free of oil and grease and particulate matter ready to be recirculated through the spray boom 23 in the subsequent cleaning cycle. To complete the fluid reclaim cycle, fluid equalization solenoid control valve 239 opens to allow the fluid levels of the three tanks 202, 203, 204 to equalize and remains open during the cleaning cycle.

The oil and grease transferred to and trapped in the discharge chamber 204 resultant of the fluid reclaim cycle is re-hydrolyzed into molecular suspension with the microbe-rich emulsifier in the discharge chamber 204. This is accomplished by diverting part of the excess volume of solution generated by the pressure pump 226 during the cleaning cycle by way of a "T" 243*c* in the primary pressure line 243.

The diverted volume is controlled by a flow valve 245 which limits a specific amount of reclaimed washing fluid to be discharged by way of a fan spray nozzle (not shown) positioned over and directed at a downward angle into the surface of the oil and grease floating in the discharge chamber 204 to agitate the fluid above the perforated plate (not shown).

When the fluid has been reclaimed, a timer located in the bioremediation unit 200 located on the roof 1 is set to activate a short, ten minute cleaning cycle during off or slow times. When the system is energized: 1. A normally closed contactor opens and disables the exhaust fan 8 to prohibit the fan from exhausting atomized cleaning solution into the atmosphere. 2. A pressure pump 226 draws suction from one of three tanks in the bioremediation unit (the circulation chamber 202) and pressurizes a low volume, low pressure spray boom assembly 23. Said assembly 23 is comprised of rotary nozzles 24 connected by pipe sections **23*b*, 23*g*, etc. (FIG. 4) and mounted vertically inside an exhaust flue 2 and horizontally along the length of any existing conventional commercial or institutional kitchen exhaust hood 5 above and behind the baffle filter bank 601. A solution of fresh water automatically mixed with a specific amount of non-toxic PH neutral surfactant/disbursant oxidizer specifically designed to promote and enhance the propagation and proliferation of microorganic life, is sprayed inside the flue and exhaust hood 2. The solution, sprayed at an extremely low pressure and volume via the special spray nozzles 24 providing complete coverage and mild impingement, is sufficient to remove the cooking oil and animal fat accumulated through a normal day's kitchen operation. The oils are in suspension or entrained in the washing fluid and drain down the baffle units 601 for collection by the gutter 700 which drains directly into the sump box 52. There, the dirty fluid is collected and returned by the sump pump 54 through the return piping system 32 installed in the hood 5 and flue 2 where it passes through the vertical section 36*e* of the fan/flue riser 36 and is emptied under pressure into the fluid collector 36*a*. There, the swirling fluid washes the grease that drains down the outer surface of the exhaust fan 8 and/or oozes out between the fan 8 and flue 2 and into fluid collector 36*a***.

All cleaning completed, the fluid then drains from the fluid collector **36*a* back into the bioremediation unit 200 (the receiver chamber 203). The receiver chamber 203 is the only tank continuously connected to the circulation chamber 202. This connection is made by a permanent pipe conduit 212 in the center portion of the chambers 202, 203. Therefore, the fluid is circulated only in the lower portion of the circulation chamber 202, which leaves any lower gravity fluid such as oil and grease virtually undisturbed, floating at the top of the tank 202**, and sediment undisturbed at the bottom.

At the completion of the timed cleaning cycle the exhaust fan contactor closes, energizing the fan 8. A metered amount of fresh, non-toxic PH neutral surfactant/ disbursement oxidizer solution contained in makeup solution injector reservoir 40 (FIG. 9) also containing a concentrated level of highly potent freshly cultured hydrocarbon-specific micro-organisms, is introduced by timed injection into the fluid return sump assembly 28, FIG. 5. During the 24 hr. interval when the cleaning solution is at rest in the bioreactive fluid reclaim unit 200, the oily pollutants separate by specific gravity and float to the surface of the tanks 202, 203, 204 where they are biodigested and converted to air, water and trace amounts of fatty acids. When the next cleaning cycle is activated, the pump 226 picks up the rejuvenated higher gravity cleaning fluid from the center level of the circulator tank 202 and cycles it through the exhaust hood/flue 5, 2 to drain into the sump assembly 28 where it combines with the new surfactant solution charged with fresh microbes at the first of each cleaning cycle. The circulation process thoroughly mixes the fluid and is thereby renewed daily.

In as much as the system takes on fresh makeup water and fresh surfactant/microbe solution daily, it must naturally, automatically discharge a certain amount of fluid as it equalizes at the full level and overflows. This is accomplished via a discharge pipe 214 connecting the discharge chamber 204 to the top of the nearest sewer drain vent stack 11, common to the kitchen floor drain system 12, 13 terminating in the main grease trap 14 integral with the sewer system (not shown). This process guarantees the automatic daily inoculation of the main grease trap 14 and sewer drain lines with microbe enriched emulsifier/ oxidizer solution to offset any negative impact as a result of the introduction of toxic chemicals into the sewer drains by kitchen staff. This completes the cleaning and bioremediation process. By utilizing this process and the system relative thereto, one is able to eliminate the need of steam cleaning commercial kitchen exhaust hoods and related costs, avoid premature roof failure, eliminate the fire hazard associated with residual grease build-up, reduce insect and rodent infestation, reduce foul odors, and greatly reduce the volume of grease accumulating in the main grease trap, thereby reducing the need for frequent pumping (grease removal) and associated costs.

Figure 10:
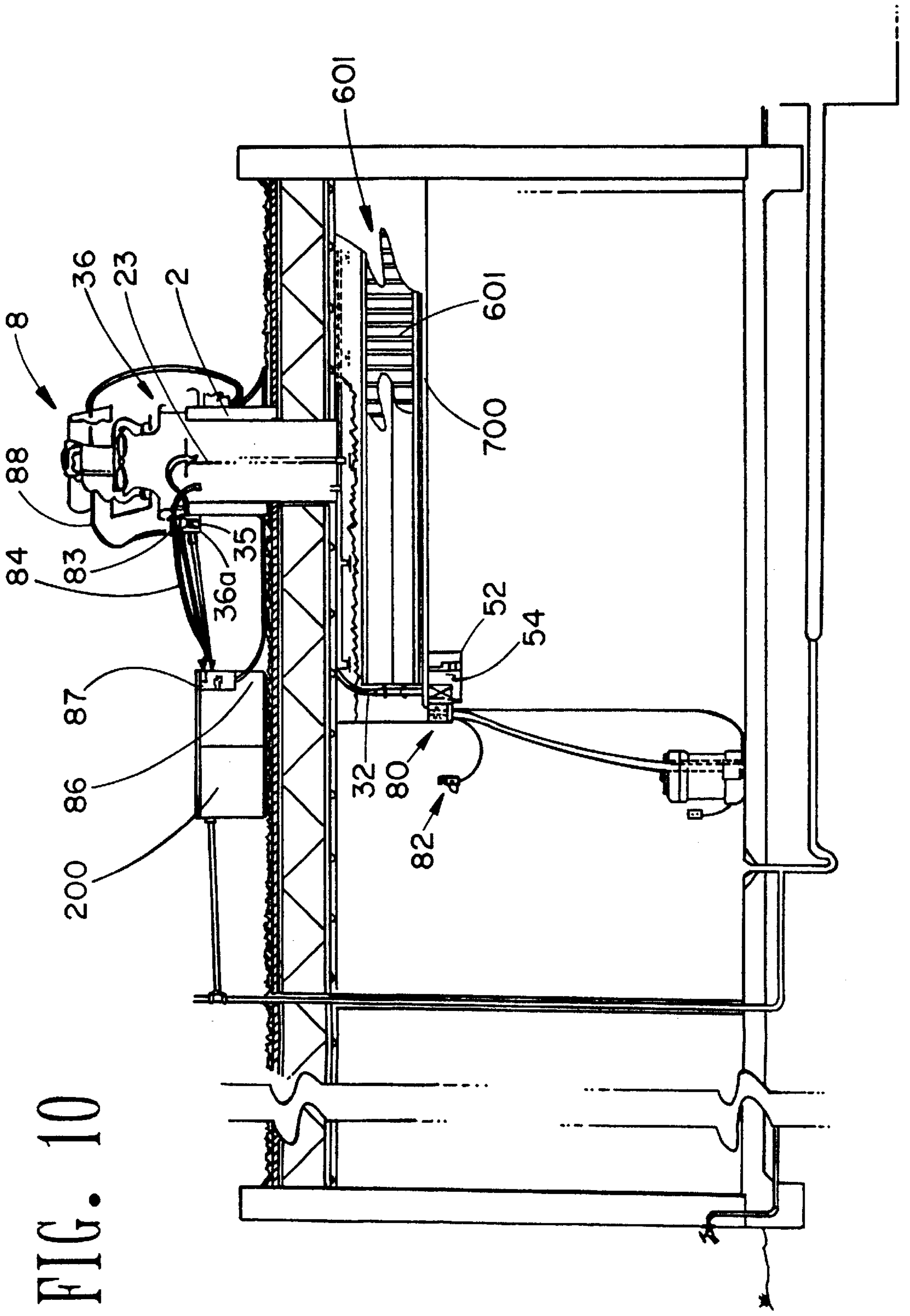
FIG. 10 is an elevational view similar to FIG. 1 but showing components of the control/monitoring system.
Figure 11:
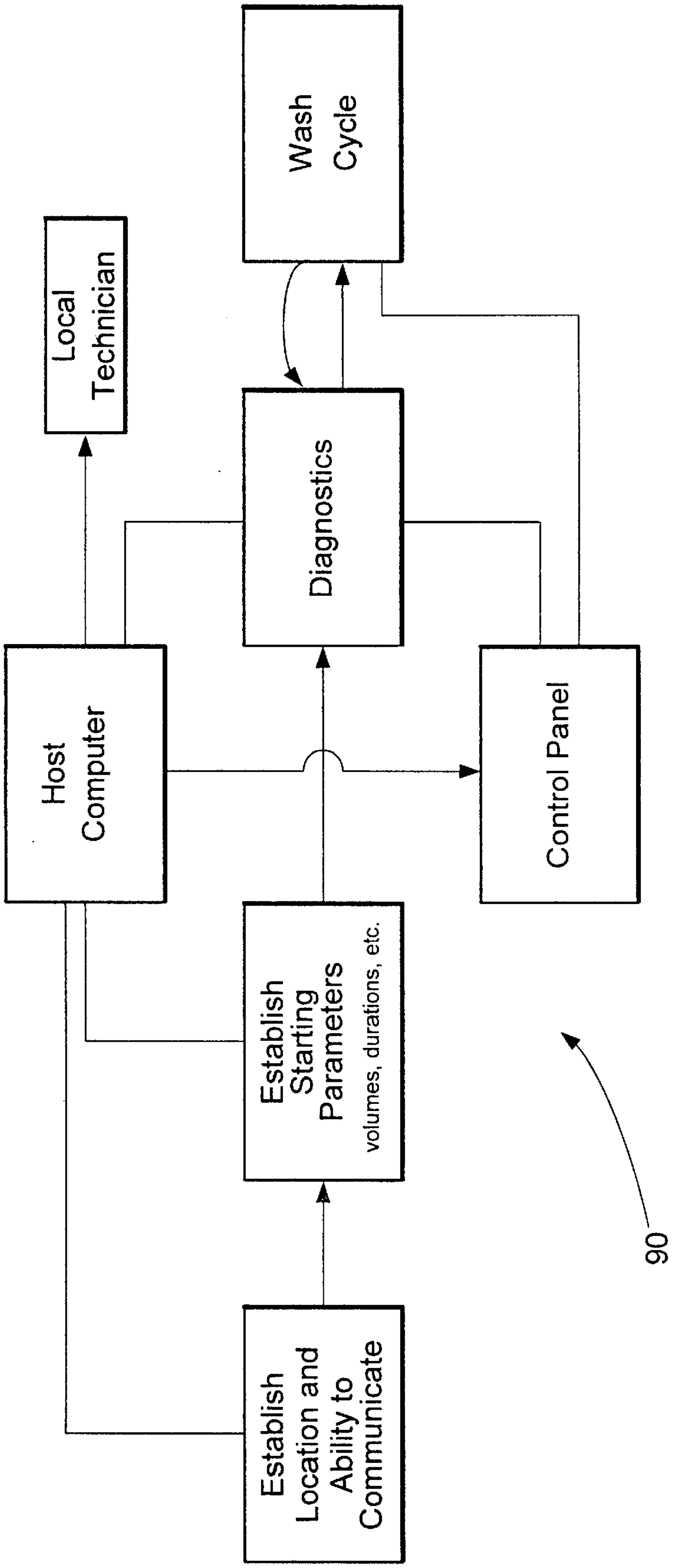
FIG. 11 is a flow diagram pertaining to the control/monitoring system.
Figure 12:
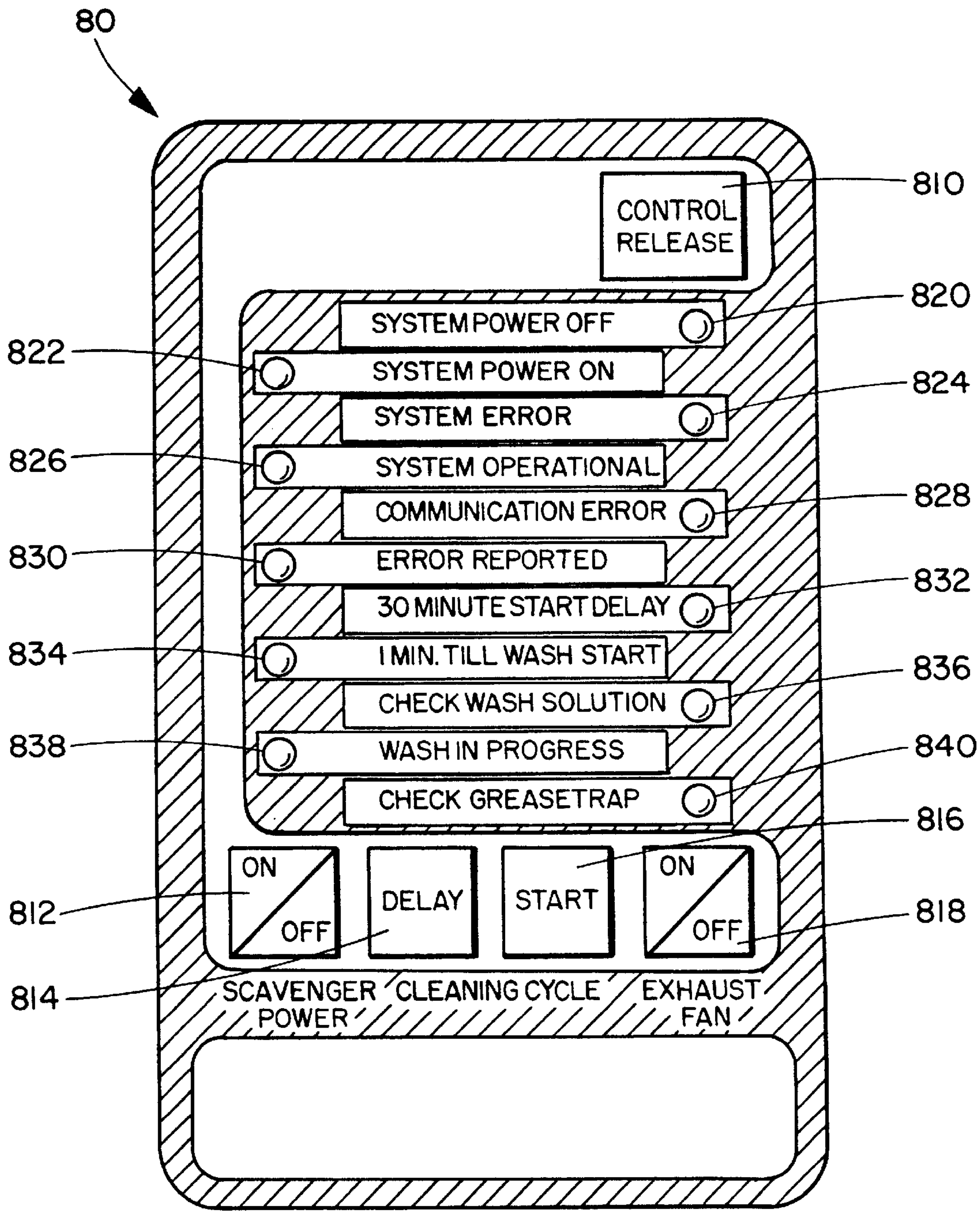
FIG. 12 is an elevational view of the control/monitoring system control pad.

The system may be improved by adding a system and method to control and monitor the kitchen grease removal and bio-remediation system. Referring to FIGS. 10–12, such a control and monitoring system 90 includes a control panel 80 which may be linked by communication lines which are preferably diode laser/fiber optics lines to other components in the system and to a host computer to automatically control and monitor the system. Communications may be established by other modes, e.g., radio signals. The fiber optics lines allow the system 90 to function as a state of the art control and monitoring system and allow the communication lines to be retrofitted into an existing kitchen by running the lines through, for example, the return piping system 32 and through the exhaust hood 4 and flue 2 which may be a hot, explosive, flammable and/or hazardous environment.

This control and monitoring system can be hooked, for example, to a modem with line to a jack 82 to the host computer. The host computer may be established to control and monitor from one to thousands of various local and remote kitchen grease remediation installations.

The control and monitoring system generally includes a master control unit 86, the control panel 80 and the host computer all of which are connected by communications lines and include sensors and actuators within the system. As mentioned above, fiber optics lines may run within the return piping system 32 to communicate with control panel 80, the make-up solution reservoir 40, the sump box 52 and the sump pump 54. These lines emerge from a "T"-fitting 83 mounted over fluid collector **36*a* and run by line 84 to the master control unit 86. The "T"-fitting 83 has one end which is the flush nozzle 35 to expel return fluid from return piping 32 into fluid collector 36*a* and two other ends, one of which connects to the return piping 32 to receive return fluid and the fiber optics lines and another end which connects to line 84. Other fiber optics line(s) 88 may run through/from "T"-fitting 83 to the exhaust fan 8 for communication with same, e.g., to turn the fan on and off as controlled by the control/monitoring system 90 or through the control panel 80. The master control unit 86 may be mounted on one end of the bioremediation unit 200. A power on/off switch 87 is connected to the master control unit 86**.

The control and monitoring system 90 at the start-up will generally first establish the location of a new system and the ability to communicate within the system and with the host computer. Then, the system will establish starting parameters for the individual system such as, for example, a volume level for the sump box 52 and the duration and frequency of a cleaning cycle. Next, the system will run diagnostics which is essentially an error reporting cycle. Permissives for the error reporting cycle are established in the system software and by the starting parameters. After the diagnostics the system is ready to initiate and conclude wash cycles. To start the wash cycle the system will stop the exhaust fan 8, allow fluid to drain and actuate valves and power the bioremediation 200. This in turn will pressurize low volume, low pressure spray boom assembly 23. In addition, the host computer may communicate with a local technician regarding potential problems or prompting a maintenance call.

The diagnostics generally include pressure sensors, liquid level sensors, temperature sensors, fluid quality sensors and power on/off devices within the system.

The diagnostics system should, by way of example, include several features as described below. The system should be able to detect the liquid level in the make-up solution reservoir 40; the system will determine whether the fluid level within the system is proper or whether the sump pump 54 is operational by detecting whether the sump pump 54 is on or off; determine whether a washing cycle completes; determine whether power comes on; actuate solenoid valves 230, 234 and 239 to start fluid flow in a washing cycle (this may be accomplished by e.g. a reed switch on the magnetic coil of the solenoid); determine whether the motor is running in the bioremediation unit 200 whether the valves are properly actuated, whether the filter is clean and whether the bioremediation unit 200 is clogged by, e.g. mounting a fluid pressure sensor at the exit from the bioremediation unit 200 to the low volume, low pressure spray boom assembly 23; prevent fluid in the system from freezing; maintain a suitable environment for microorganisms within the system and enhance hydrocarbon emulsification by having temperature sensors primarily in the bioremediation unit 200 which in turn may cause the heaters in the bioremediation unit 200 to cycle on or off; to detect or meter how much fluid is dumped from the bioremediation unit 200; to accumulate data and determine the duration and frequency of the cleaning cycle and of scheduled maintenance (e.g. initially the system parameters may define the wash cycle as running two minutes every twenty-four hours, but accumulated data may dictate more or less frequent cycles and/or longer or shorter durations); to detect the fluid level in the bioremediation unit 200; turn pumps on/off (e.g. micro-organism aeration pump); communicate with control panel 80. The construction of such a system is within the level of one of ordinary skill in the art.

Referring to FIG. 12, the control panel 80 for the control/monitoring system is shown. The control panel 80 generally includes manual override buttons and various displays which in this embodiment are "labeled" LED displays. More than one color of LED may be used to communicate various messages as would be appreciated by one skilled in the art. The control panel 80 includes in this embodiment a control release button 810 which may be used in combination with the other buttons to be described, a system on/off button 812, a cleaning cycle delay button 814, a cleaning cycle start button 816 and an exhaust/vent fan on/off button 818. The following LEDs with "labeling" may be included; system power off 820, system power on 822, system error 824, system operational 826, communication error 828, error reported 830, 30 minute start delay 832, 1 minute until wash cycle starts 834, check wash solution 836, wash in progress 838 and check greasetrap 840. Other displays and operational bottoms may be incorporated.

Other options/improvements are described below. The bioremediation unit 200 may be moved from the roof to be mounted inside the commercial kitchen or on the ground outside the commercial kitchen.

The baffle filter units 601 may be coated with TEFLON. The baffle filter units 601 may also be constructed with a "clamshell" feature allowing one to "fold" the baffle filter units 601 open for cleaning the return legs **620*a* and 620*b* and the interior of the baffle filter units 601 in general. The baffle filter units 601** may then be closed for use in the vent hood.

An oil/grease skimmer may be retrofitted to the system, for example, an off the shelf skimmer may be mounted over the existing grease trap in a perforated pipe and include a pump for pumping grease to a drum (all not shown) mounted in the commercial kitchen. A drain line 11 can run to the skimmer.

The fan/flue riser 36 can be constructed to be telescoping, as known to one skilled in the art. This allows the fan/flue riser 36 to be adapted/retrofitted and mounted to existing flues of various sizes.

The weirs **206*a*, 206*b* may be replaced by a single weir (not shown) which is central, integral and common to all three tanks 202, 203, 204 in the bioremediation unit 200. The single weir is similar to the weirs 206*a*, 206*b*** in its operation.

What is claimed is:

1. An apparatus for bioremediating a fluid entrained with grease from a kitchen, comprising:

a discharge chamber;

a receiver chamber connected to the discharge chamber by a first flow line;

a circulation chamber connected to the discharge chamber by the first flow line;

a pump contained in the first flow line;

a first valve connected in the first flow line;

a first means for stratifying the fluid contained inside the circulation chamber;

a second means for stratifying the fluid contained inside the receiver chamber;

a second flow line connected between the receiver chamber and the circulation chamber;

a first weir having one end connected near the top level of the circulation chamber and another connected to terminate in the discharge chamber;

a second weir having one end connected near the top level of the receiver chamber and another end connected to the discharge chamber;

a means for removing reclaimed fluid from the circulation chamber attached to the circulation chamber;

a means for adding fluid to be remediated to the receiver chamber attached to the receiver chamber;

an equalization line connecting the receiver chamber to the discharge chamber; and a second valve contained in the equalization line.

* * * * *